United States Patent

Long et al.

Patent Number: 5,154,708
Date of Patent: Oct. 13, 1992

[54] UNITARY SCALPEL FOR CONTACT LASER SURGERY

[75] Inventors: Gary L. Long, Cincinnati, Ohio; James R. Tobias, Florence, Ky.; John C. Vanden Hoek, Elk River, Minn.

[73] Assignee: Surgical Laser Technologies, Inc., Malvern, Pa.

[21] Appl. No.: 678,170

[22] Filed: Mar. 29, 1991

Related U.S. Application Data

[63] Continuation-in-part of Ser. No. 523,884, May 15, 1990, abandoned.

[51] Int. Cl.⁵ .............................................. A61B 17/36
[52] U.S. Cl. ...................................... 606/16; 128/395
[58] Field of Search ............................ 606/2, 13–16; 128/395–398

[56] References Cited

U.S. PATENT DOCUMENTS

| | | | |
|---|---|---|---|
| 3,467,098 | 9/1969 | Aysis | 128/395 |
| 3,834,391 | 9/1974 | Block | 128/303.1 |
| 4,170,997 | 10/1979 | Pinnaw et al. | 606/16 |
| 4,576,177 | 3/1986 | Webster | 606/15 |
| 4,592,353 | 6/1986 | Daikuzono | 128/303.1 |
| 4,592,353 | 4/1989 | Daikuzono | 128/303.1 |
| 4,693,244 | 9/1987 | Daikuzono | 128/303.1 |
| 4,736,743 | 4/1988 | Daikuzono | 128/303.1 |

FOREIGN PATENT DOCUMENTS

| | | |
|---|---|---|
| 2821265 | 5/1978 | Fed. Rep. of Germany . |
| 2826383 | 6/1978 | Fed. Rep. of Germany . |
| WO90/01907 | 8/1989 | PCT Int'l Appl. . |
| 2154761 | 2/1985 | United Kingdom . |

Primary Examiner—Max Hindenburg
Attorney, Agent, or Firm—Seidel, Gonda, Lavorgna & Monaco

[57] ABSTRACT

A unitary contact laser scalpel for orthopedic or other operative procedures. The scalpel comprises a tapered conical member in part of ceramic or similar material characterized by high strength and low coefficient of thermal conductivity. A cylindrical passage is formed along and through the central axis of the ceramic member into which an optical fiber is secured. The distal end of the optical fiber may be oriented flush with the tapered end of the conical member or it may define a tapered extension of the ceramic material. The tapered end of the conical member may have a narrow diameter generally in the order of twice that of the optical fiber and may be coated with an enamel material. Alternatively, a larger diameter optical fiber may be employed with the combination of ceramic and fiber being formed as a conical contour.

5 Claims, 2 Drawing Sheets

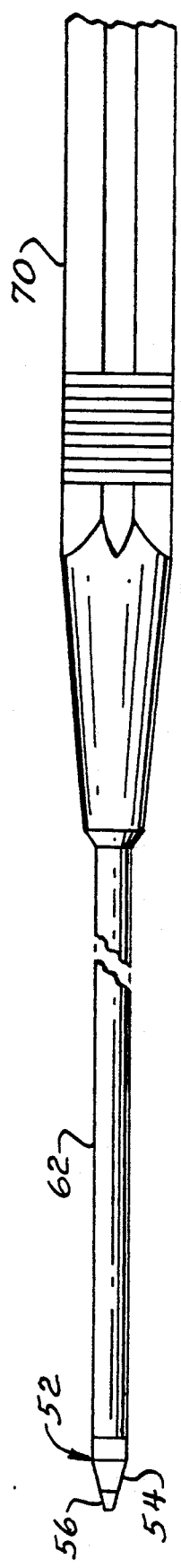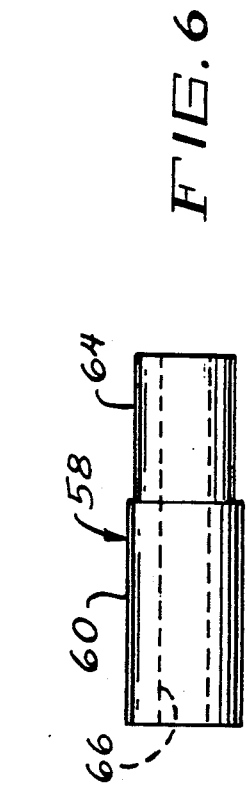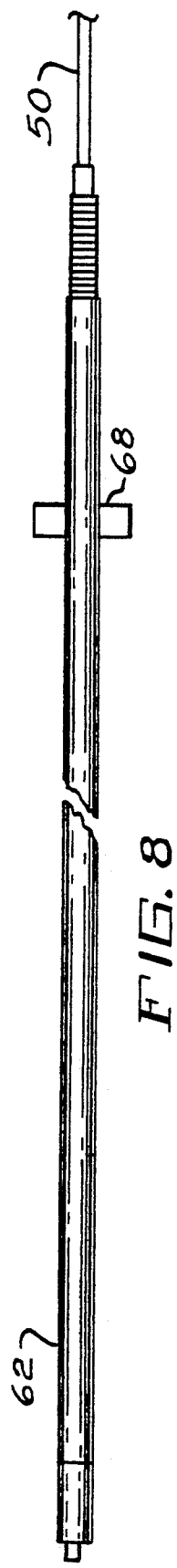

UNITARY SCALPEL FOR CONTACT LASER SURGERY

BACKGROUND OF THE INVENTION

This is a continuation-in-part application of Ser. No. 07/523,884, filed on May 15, 1990, now abandoned.

The present invention relates to scalpels for contact laser surgery, in particular, to scalpels intended for use in conjunction with, or as an integral member of, a flexible optical fiber delivery system. Such delivery systems are generally used, for example, with Nd:Yag and other lasers of wavelength suitable the for efficient transfer of laser energy through an optical fiber medium.

The present scalpel finds particular application in orthopedic surgery, for example, in the removal of damaged meniscus from the knee. The operative situs for such a procedure is commonly and preferably surrounded by water. This presence of water, however, creates significant problems for contact laser scalpels of conventional design.

More specifically, the tip region of the contact scalpel necessarily heats following any sustained interval of cutting. As the scalpel is removed, the heated tip is suddenly exposed and emersed in the relatively cool liquid surrounding the cut location thereby causing a corresponding rapid cooling of the tip. This cooling has been known to weaken or even fracture the sapphire or other crystalline material of which conventional laser scalpels are fabricated.

The contact laser scalpel of the present invention has been developed to overcome this and certain other known problems associated with conventional non-unitary scalpel configurations.

With specific reference to the above-mentioned fracturing problem, the present scalpel does not utilize conventional sapphire or similar optically transparent contact members—at least, not in such configuration as to expose the material to the rigors of extreme temperature cycling. Rather, the optically active elements of the present invention are at least partially encased within, and protected by, an opaque ceramic ferrule, preferably of alumina, which material exhibits numerous advantageous properties with particular reference to aqueous environments.

First, the coefficient of thermal conductivity of alumina is quite low. As a consequence, the heat which is generated at the distal tip end region of the probe is not propagated along the probe and handle and therefore does not ordinarily heat non-active portions of the scalpel system. Nor, in the case of the narrow fiber embodiment of the present invention, is this heat communicated to the ferrule core where such fiber is located.

Further, by limiting the conduction of heat energy to non-productive regions of the scalpel, proper scalpel operations can be maintained at lower overall laser power levels. Additional reductions in the laser power requirements may be realized through the elimination of the fiber-to-scalpel interface discussed in more detail below.

A further and very significant property of alumina is its resistance to thermal shock-induced fracturing. This problem is particularly acute, as noted, in certain orthopedic applications where the scalpel must be withdrawn from the meniscus through its surrounding fluid environment.

Yet another advantage of alumina is its intrinsic strength. Alumina has been found to exhibit greater tolerance to the lateral sheer loads to which a scalpel is invariably subjected during any cutting procedure.

The alumina ferrule is not, however, an active element of the scalpel in an optical sense. Indeed, alumina and most similar ceramic materials are opaque to the laser wavelengths of interest. In the narrow fiber embodiment of the present invention, optical focusing of the laser energy to the tip end region of the scalpel is achieved by placement of a narrow optical fiber within the ferrule, along the central axis thereof. This fiber is of uniform diameter and is preferably formed as an extension, in whole or in part, of the delivery system optical fiber, i.e. the fiber through which the laser energy is conveyed from the laser to the operative situs.

In an alternative embodiment, a fiber of greater diameter is employed with the fiber and ceramic ferrule combination being ground or otherwise machined to form a tapered conical profile. In this latter arrangement, the fiber will be seen to extend forwardly of the reinforcing ceramic ferrule.

It will be appreciated that the present scalpel provides, in addition to the above-enumerated advantages associated with the ceramic ferrule itself, the elimination of the interface between fiber and scalpel contact member. This advantage may be realized with either the narrow or wider tapered fiber embodiments of the present invention.

This interface represents a perennial problem area in contact laser probe and scalpel implementation. The threaded connectors which affix the scalpel implementation. The threaded connectors which affix the scalpel to the fiber optic delivery system must be of accurate design, thread, placement, and construction in order to assure proper alignment between the delivery fiber and the scalpel. Not only are the metallic couplings expensive, but their retention often requires grooves or other indentations in the sapphire thereby causing potential stress breakage points.

But most importantly, associated with any coupling of laser energy from one medium to another are the inherent coupling losses. These losses translate directly into heat generated at coupling interface which, in turn, must be conducted away from this interface if sustained scalpel operation, particularly at higher power levels, is contemplated.

It is therefore a significant advantage of the present scalpel arrangement that the delivery system to scalpel interface may be eliminated, or at least remotely positioned relative to the operative situs.

It is well known, however, that the angle of dispersion from the end of a bald, unfocused optical fiber is generally rather narrow, e.g. about 10 degrees, and therefore is not appropriate for many surgical applications. By comparison, the dispersion angle for conventional sapphire contact laser probes is approximately 25–35 degrees.

The narrow fiber embodiment of the present scalpel overcomes these restrictions by limiting the diameter of the ceramic ferrule in the tip end region, preferably to about twice the fiber diameter or less. Further, the fiber is extended into flush relationship with the distal end of the ceramic thereby permitting or causing the corresponding distal end of the fiber to, as presently understood, partially liquify and/or recrystallize, in turn, resulting in a wider energy dispersion profile.

It will therefore be apparent that the ceramic ferrule serves these additional functions including the support of the otherwise highly flexible fiber as well as the maintenance of the integrity of the distal portion of such fiber when the latter is subjected to the elevated temperature regime associated with actual scalpel operation.

In the case of the wider fiber embodiment of the present invention, the fiber itself generally defines a tapered conical extension from the ceramic ferrule and serves to contain or focus the laser energy to the tip end of the tapered fiber as taught, for example, in U.S. Pat. No. 4,693,244, owned by the present applicant.

In yet another embodiment of the present invention, an optically transparent enamel is baked onto the surface of scalpel, generally from the tip region back between 1 and 2 mm. This coating may advantageously contain infrared absorbing material as taught in U.S. Pat. No. 4,736,743, although such is not required for the practice of this invention. Thus, the several structural relationships noted above, either alone or in combination with the enamel coating, give the present extended-fiber ceramic scalpel improved laser dispersion and scalpel side cutting characteristics.

These and other advantageous and objects of the present invention will become apparent from the following drawings, detailed description of the invention, and claims.

BRIEF DESCRIPTION OF THE DRAWINGS

FIG. 5 is a front elevation view of the wider fiber embodiment of the present invention;

FIG. 6 is a front elevation view of the ceramic ferrule used in connection with the scalpel of FIG. 5 prior to the assembly and conical machining thereof;

FIG. 7 is a front elevation view of a partially assembled scalpel of FIG. 5 illustrating the positioning of the unmachined ceramic ferrule on the optical fiber; and, FIG. 8 is a front elevation view of a partially assembled scalpel of FIG. 5 shown with the metal wand in position prior to the machining of the ceramic and fiber.

DESCRIPTION OF THE PREFERRED EMBODIMENT

Figure 1:
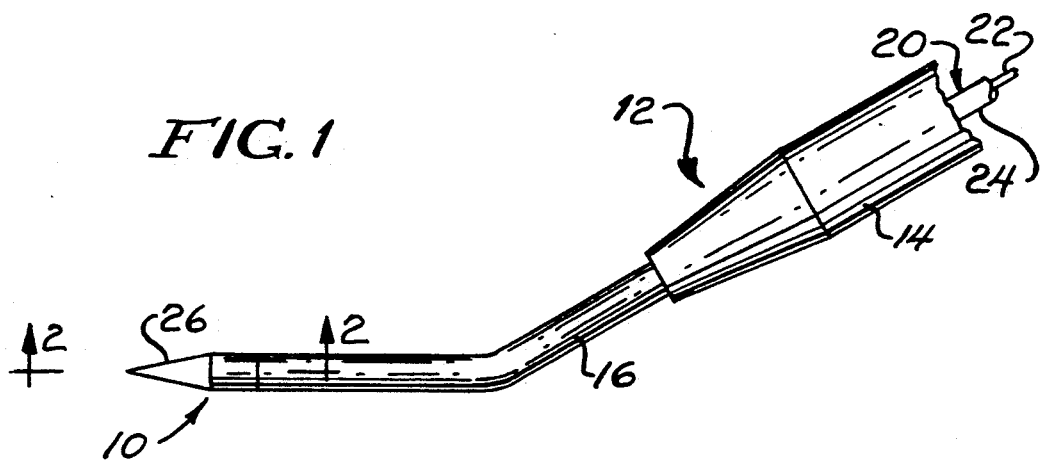
FIG. 1 is a front elevation view of the narrow fiber embodiment of the ceramic laser scalpel of the present invention shown affixed to handpiece.

Referring to FIG. 1, the narrow fiber contact laser ceramic scalpel 10 of the present invention is shown positioned at the distal end of a surgical handpiece 12. Handpiece 12 is of conventional design having a widened body portion or handle 14 with a tubular member or wand 16 extending therefrom.

A channel or opening 18 (FIG. 2) is provided in the handpiece through which an optical fiber system 20 passes. This system is also of known design and includes an optical fiber 22, preferably of fused silica, through which the laser energy is channelled and a protective sheathing 24 concentrically thereon.

Although optical fibers of varying diameters are found in connection with known contact laser probes and scalpels, a fiber of relatively narrow diameter, for example 200 microns, is preferred for the present extended-fiber ceramic scalpel—this by reason that the delivery system fiber extends through, and thereby defines, the entire optical path of the scalpel itself.

The present scalpel includes a tapered or conically-shaped ferrule 26 fabricated from a ceramic material of high sheer strength and low thermal conductivity. Alumina has been found to be satisfactory and is preferred in view of its extremely low thermal conductivity (0.07 cal/cm.sec.° C.) and its proven resistance to mechanical failure under ordinary surgical conditions.

As noted, the present ceramic scalpel 10 is positioned and affixed to the distal end of the handpiece wand 16. More specifically, the rear or input portion 28 of the ferrule is machined, or molded, to a diameter generally equal to the inside dimension of the tubular member thereby permitting the ferrule to be snugly received therein. The diameter of the cylindrical body portion 30 of the ferrule is preferably the same as that of the wand 16 thereby defining a smooth, even transition between the scalpel and handpiece.

Figure 3:
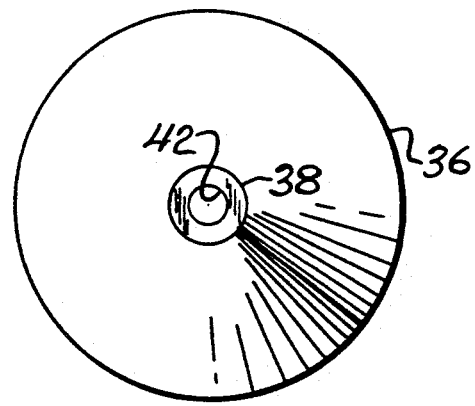
FIG. 3 is a left side elevation view of the ceramic scalpel of FIG. 1.

The forward scalpel region 32 is of conical profile having, in one preferred arrangement, a taper angle of approximately 8 degrees. This taper extends from its widest diameter generally, as noted, equal to that of the tubular member, to a narrow cross-section at the scalpel tip end 34 preferably in the order of twice the diameter of the fiber or, in the present case, to a diameter of 400 microns. The enlarged side elevation or end view of FIG. 3 illustrates the cylindrical body, the narrow tip, and fiber diameters, respectively, as 36, 38, and 40.

It will be appreciated that other taper angles and tip end diameters 38 may be utilized. However, proper scalpel cutting action may be comprised as the tip end diameter is increased. Tip diameters in excess of 3 or 4 times that of the fiber are not, as presently understood, suitable.

Figure 2:
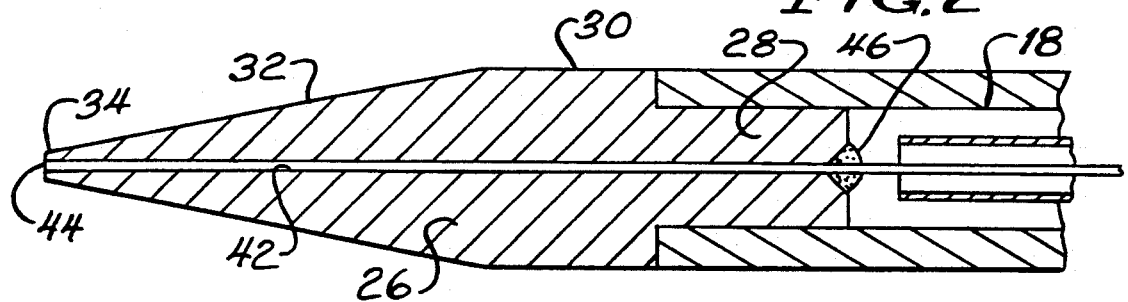
FIG. 2 is a sectional view of the ceramic laser scalpel taken along line 2—2 of FIG. 1.

A hole or passage 42 is provided along the longitudinal scalpel axis through which an extended portion of fiber 22 is passed. This hole is of appropriate diameter to snugly receive fiber 22 therein, although retention of the fiber within the scalpel may be assured by, for example, epoxying the fiber to the rear portion of the scalpel as shown at 46 (FIG. 2). The distal end 44 of this fiber is positioned, or cleaved, flush with the scalpel tip end 34.

Various fabrication techniques are contemplated for the present ferrule including machining, molding, and drawing or extrusion. Presently, the preferred manner of manufacture is by drawing or extruding the ferrule with a pin member in the die to form the axial fiber passage 42.

It will be appreciated that the present extended fiber scalpel provides for the transmission of the laser energy from the laser source (not shown) to the point of operative tissue contact (i.e. at the scalpel tip end 34) along a single continuous fiber path without the fiber-to-scalpel interface ordinarily found in other contact laser instruments. Such interfaces necessarily exhibit losses which, in turn, require cooling or restricted operating regimes to limit unacceptable heat concentrations.

Thus, the present scalpel provides conventional cutting action, and does so in the hostile liquid-filled environment characteristic of orthopedic surgery, while simultaneously exhibiting improved strength, fracture resistance, and little or no requirement for scalpel cooling.

Alternatively, a connector may be provided to permit removal of the scalpel and/or handpiece from the laser delivery system optical fiber, but, at a spaced, remote location from the scalpel. In this manner, fibers and scalpels may be exchanged or replaced as required without having to place an optical fiber-to-scalpel interface adjacent the operative site.

Bare optical fibers of conventional design, for example the 200 micron fiber 22 of the present scalpel, ordinarily exhibit radiation divergence angles which are too narrow for surgical applications—typically in the order of about 8 degrees. Divergence angles of between two and three or more times that of a bare fiber are considered standard for best scalpel operation.

The present structure, however, does not exhibit the narrow divergence characteristic of conventional bare fibers. Use of the low thermal conductivity ferrule, with its relatively narrow cross-section in the tip end region, and the partial exposure of the optical fiber at the scalpel tip end 34 combine to create a scalpel of wider laser divergence.

As presently understood, the ceramic material at the extreme scalpel tip end locally heats due, as noted, to its narrow cross-section and low thermal conductivity. This heating, in combination with the exposed nature of the fiber tip itself, is believed to cause a slight structural realignment or bubbling of the fiber tip which, in turn, results in a greater laser radiation divergence angle.

It will be appreciated, therefore, that the ceramic ferrule serves several important functions. In addition to the above-described interaction of the ferrule and fiber (i.e. to increase the divergence angle), the ferrule provides the necessary strength and rigidity to an otherwise flexible fiber and, importantly protects the fiber against undue thermal deterioration.

In this later connection, it is well known that exposed fibers, when brought into prolonged direct contact with tissue, are subject to melting and other forms of physical destruction. Thus, the narrowed tip region of the ceramic ferrule provides the requisite strength and protection of the optical fiber while simultaneously cooperating in the limited restructuring of the fiber which, in turn, facilitates increased laser divergence.

Figure 4:
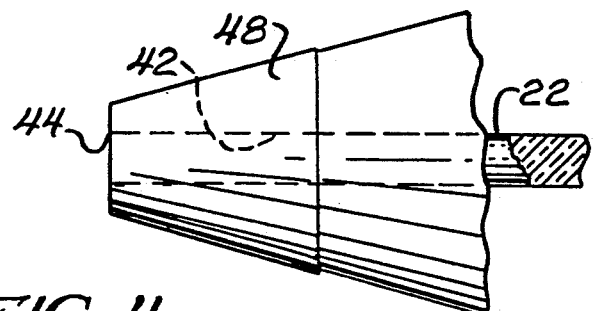
FIG. 4 is an enlarged fragmentary front elevation view of the tip end region of the ceramic scalpel of FIG. 1 illustrating the enamel coating thereon.

FIG. 4 illustrates another embodiment of the present invention adapted to further enhance the laser divergence angle. In this arrangement, the tip end of the scalpel described above (FIGS. 1-3) is dipped in an enamel silica paste and thereafter baked to cure or harden the coating 48. The enamel coating improves scalpel cutting by further enhancing the laser divergence angle and by conducting heat energy through the coating thereby to create limited side heating in the tip end region of the scalpel.

The enamel coating is applied to the tip end region, typically covering about 1½ mm, although extended or more restricted applications may be applied to create scalpels having correspondingly differing side cutting characteristics.

FIGS. 5-8 illustrate yet another embodiment of the present scalpel employing a wider diameter optical fiber 50, for example 1000μ. Like the previously described scalpels, the present embodiment preferably employs a continuous fiber that interconnects the source of laser energy with the operative situs. In this manner, additional laser energy interfaces may be avoided.

As previously described, the ceramic ferrule 52 defines a tapered, conical profile 54. However, due to the incorporation of an increased diameter 1000μ optical fiber, the ferrule cannot be machined to narrow point. Rather, as set forth more fully hereinafter, the ceramic ferrule and optical fiber or jointly machined to form an overall tapered, conical profile in which the distal end of the optical fiber 56 is, itself, tapered and thereby extending forwardly of the ferrule to define a surgical cutting surface.

FIG. 6 depicts the ceramic ferrule blank 58 prior to assembly and machining into its tapered form. Ferrule blank 58 is of cylindrical cross-section having, as previously described, an outer diameter 60 generally equal to that of the supporting wand 62 (FIGS. 5 and 8) and a narrower diameter portion 64 adapted for insertion into the distal end of the tubular wand 62. In one preferred arrangement the unmachined blank is approximately 0.31 inches in length.

An aperture 66 is provided along the longitudinal axis of the ferrule blank through which the optical fiber is passed. More specifically, and referring to FIG. 7, the ceramic ferrule blank 58 is slipped onto the optical fiber 50 after approximately ⅜ inch of cladding has been removed therefrom. The blank is held in position by an expoxy, for example, No. 353. Thereafter the tubular wand 62 is slipped and epoxied into position as shown in FIG. 8.

Wand 50 includes a wing member 68 rigidly affixed thereto. This member is within the plastic housing or handle 70 thereby precluding the angular movement of the wand with respect to the handle. This is particularly important where offset or angled wands of the type illustrated at 16 in FIG. 1 are employed.

The assembled wand/fiber/ferrule of FIG. 8 is thereafter placed, for example, in a spin fixture where a diamond wheel machines the requisite taper into the distal end of the scalpel, in particular, into the assembled ceramic ferrule and optical fiber combination thereby forming the tapered ferrule and fiber surfaces respectively at 54 and 56 of FIG. 5. The tapered end of the optical fiber may thereafter be roughened, by bead blasting or otherwise, to facilitate adhesion of an infrared coating material as set forth in U.S. Pat. No. 4,736,743.

It will be appreciated that the above-described wide-diameter scalpel also represents a strong and substantially inflexible surgical instrument—such structural integrity being attributable to the combination of the inherent strength of the 1000μ fiber and, importantly, the ceramic ferrule support member.

We claim:
1. A contact laser scalpel for orthopedic and other surgical applications including a rigid support member, the support member having an opening extending therethrough from a first proximal end to a second distal operative end, at least a portion of said support member at said operative end being of a ceramic material; an elongate optical laser energy conductor, the laser conductor having a laser energy inlet and a laser energy irradiation outlet, said irradiation outlet defining contact surface means for direct engagement with operative material, the laser conductor being positioned within the support member opening and being oriented whereby the laser irradiation outlet is substantially coincident with the distal operative end of the support member; the laser energy conductor having a length greater than the opening in the support member, the conductor thereby extending outwardly from the support member with the conductor inlet being spaced remotely from the support member proximal end whereby there are no laser energy interfaces and couplers proximal to the contact surface means and whereby the interface and coupling of laser energy into the inlet end of the conductor is displaced from the laser scalpel support member thereby avoiding coupling losses and the corresponding requirement for cooling immediately proximal to the scalpel support member.

2. A contact laser scalpel for orthopedic and other surgical applications including a rigid support member, the support member having an opening extending therethrough from a first proximal end to a second distal end, at least a portion of said support member at said operative end being of a ceramic material; an elongate optical fiber for conducting laser energy from a laser source to an operative situs, the fiber having a laser energy inlet for connection to the source of laser energy and a laser energy irradiation outlet, said irradiation outlet defining contact surface means for direct engagement with operative material, the fiber being positioned within the support member opening and being oriented whereby the laser irradiation outlet is substantially coincident with the distal operative end of the support member; the fiber inlet extending from the proximal end of the support member whereby the fiber inlet may be coupled to the laser source remote from the support member and whereby there are no laser energy interfaces and couplers proximal to the contact surface means thereby avoiding coupling losses and the corresponding requirement for cooling at the scalpel support member.

3. A contact laser scalpel for orthopedic and other surgical applications including a rigid ceramic support member, the support member having an opening extending therethrough from a first proximal end to a second distal operative end; an elongate optical laser energy conductor of generally uniform cross-section, the laser conductor having a laser energy inlet and a laser energy irradiation outlet, the laser conductor being positioned within the support member opening and being oriented whereby the laser irradiation outlet is substantially coincident with the distal operative end of the support member; an enamel silica coating on the distal end of the support member and optical conductor thereby enhancing scalpel side-cutting and irradiation angle.

4. A contact laser scalpel for orthopedic and other surgical applications including a rigid support member, the support member having an opening extending therethrough from a first proximal end to a second distal end; an elongate optical laser energy conductor, the laser conductor having a laser energy inlet and a laser energy irradiation outlet, the laser conductor being positioned within the support member opening and extending forwardly therefrom; the support member and outlet end of the optical conductor being tapered in diameter whereby said outlet end of the optical conductor defines a contact surface for engaging operative material and whereby the tapered support member structurally reinforces and protects said conductor.

5. A contact laser scalpel for orthopedic and other surgical applications including a rigid support member, the support member having an opening extending therethrough; an elongate optical laser energy conductor of generally uniform diameter, the laser conductor having a laser energy inlet and a laser energy irradiation outlet, the laser conductor being positioned within and extending through the support member opening; the support member and outlet end of the optical conductor being tapered in diameter, the diameter of the outlet end of the optical conductor being less than that of the fiber itself whereby said outlet end of the optical conductor extends forwardly from the support member and defines a contact surface for engaging operative material and whereby the tapered support member structurally reinforces and protects said optical conductor.

* * * * *

UNITED STATES PATENT AND TRADEMARK OFFICE
CERTIFICATE OF CORRECTION

PATENT NO. : 5,154,708
DATED : October 13, 1992
INVENTOR(S) : Long et al.

It is certified that error appears in the above-indentified patent and that said Letters Patent is hereby corrected as shown below:

Column 1, line 13: "the for" should read --for the--.

Column 2, line 3: "sheer" should read --shear--.

Column 4, line 7: "sheer" should read --shear--.

Column 6, line 3: "or" should read --are--.

Signed and Sealed this

Fourth Day of January, 1994

Attest:

BRUCE LEHMAN

Attesting Officer   Commissioner of Patents and Trademarks